(12) United States Patent
Maniar

(10) Patent No.: US 11,382,877 B2
(45) Date of Patent: *Jul. 12, 2022

(54) FORMULATION OF (E)-2,4,6-TRIMETHOXYSTYRYL-3-[(CARBOXYMETHYL)AMINO]-4-METHOXYBENZYLSULPHONE WITH ENHANCED STABILITY AND BIOAVAILABILITY

(71) Applicant: ONCONOVA THERAPEUTICS, INC., Newtown, PA (US)

(72) Inventor: Manoj Maniar, Fremont, CA (US)

(73) Assignee: ONCONOVA THERAPEUTICS, INC., Newtown, PA (US)

( * ) Notice: Subject to any disclaimer, the term of this patent is extended or adjusted under 35 U.S.C. 154(b) by 265 days.

This patent is subject to a terminal disclaimer.

(21) Appl. No.: 16/604,978

(22) PCT Filed: Apr. 13, 2018

(86) PCT No.: PCT/US2018/027514
§ 371 (c)(1),
(2) Date: Oct. 11, 2019

(87) PCT Pub. No.: WO2018/191634
PCT Pub. Date: Oct. 18, 2018

(65) Prior Publication Data
US 2021/0186902 A1    Jun. 24, 2021

Related U.S. Application Data

(63) Continuation-in-part of application No. 15/688,320, filed on Aug. 28, 2017, now Pat. No. 10,098,862, and a continuation-in-part of application No. PCT/US2017/048890, filed on Aug. 28, 2017.

(60) Provisional application No. 62/485,355, filed on Apr. 13, 2017.

(51) Int. Cl.
| | | |
|---|---|---|
| *A61K 31/145* | (2006.01) | |
| *A61K 47/10* | (2017.01) | |
| *A61K 9/00* | (2006.01) | |
| *A61P 35/02* | (2006.01) | |
| *A61K 9/48* | (2006.01) | |

(52) U.S. Cl.
CPC .......... *A61K 31/145* (2013.01); *A61K 9/0053* (2013.01); *A61K 9/4858* (2013.01); *A61K 47/10* (2013.01); *A61P 35/02* (2018.01)

(58) Field of Classification Search
CPC .. A61K 31/145; A61K 31/196; A61K 31/198; A61K 9/0019; A61K 9/0053; A61K 9/4858; A61K 9/4866; A61K 47/10; A61P 35/00; A61P 35/02
See application file for complete search history.

(56) References Cited

U.S. PATENT DOCUMENTS

| | | |
|---|---|---|
| 8,063,109 B2 | 11/2011 | Bell |
| 8,476,320 B2 | 7/2013 | Maniar |
| 10,098,862 B1 | 10/2018 | Maniar |
| 2015/0313859 A1 | 11/2015 | Maniar |

OTHER PUBLICATIONS

International Search Report issued in PCT/US2018/027514 dated Feb. 7, 2019 (7 pages).
Written Opinion issued in PCT/US2018/027514 dated Feb. 7, 2019 (12 pages).
Bowles et al., "Phase I Study of Oral Rigosertib (ON 01910.Na), a Dual Inhibitor of the PI3K and Plk1 Pathways, in Adult Patients with Advanced Solid Malignancies", Clin Cancer Res. Mar. 15, 2014;20(6): 1656-65. doi: 10.1158/1078-0432.CCR-13-2506.
Olnes et al., "Directed therapy for patients with myelodysplastic syndromes (MDS) by suppression of cyclin D1 with ON 01910. Na", Leuk Res. Aug. 2012;36(8):982-9. doi: 10.1016/j.leukres.2012.04.002.
Raza et al., "Oral Rigosertib (ON 01910.Na) Treatment Produces A Encouraging Rate Of Transfusion Independence In Lower Risk Myelodysplastic Syndromes (MDS) Patients; A Genomic Methylation Profile Is Associated With Responses", Blood (2013) 122 (21): 2745.
Navada et al., "Combination of Oral Rigosertib and Injectable Azacitidine in Patients with Myelodysplastic Syndromes (MDS): Results from a Phase II Study", Blood (2016) 128 (22): 3167.
Navada et al., "A Phase II Study of the Combination of Oral Rigosertib and Azacitidine in Patients with Myelodysplastic Syndromes (MDS)", Blood (2014) 124 (21): 3252.
Komrokji et al., "Phase I clinical trial of oral rigosertib in patients with myelodysplastic syndromes", Br J Haematol. Aug. 2013;162(4):517-24. doi: 10.1111/bjh.12436.
Written Opinion issued in PCT/US2018/027514 on Aug. 20, 2019 (11 pages).

*Primary Examiner* — Sarah Pihonak
(74) *Attorney, Agent, or Firm* — Wolff IP a Prof Corp; Jessica Wolff

(57) ABSTRACT

Pharmaceutical compositions of (E)-2,4,6-trimethoxystyryl-3-[(carboxymethyl)amino]-4-methoxybenzylsulphone and pharmaceutically acceptable salts thereof are described as well as methods of their use, and a dose regimen of (E)-2,4,6-trimethoxystyryl-3-[(carboxymethyl)amino]-4-methoxybenzylsulphone, sodium salt to reduce the incidence of urothelial toxicity.

14 Claims, 2 Drawing Sheets

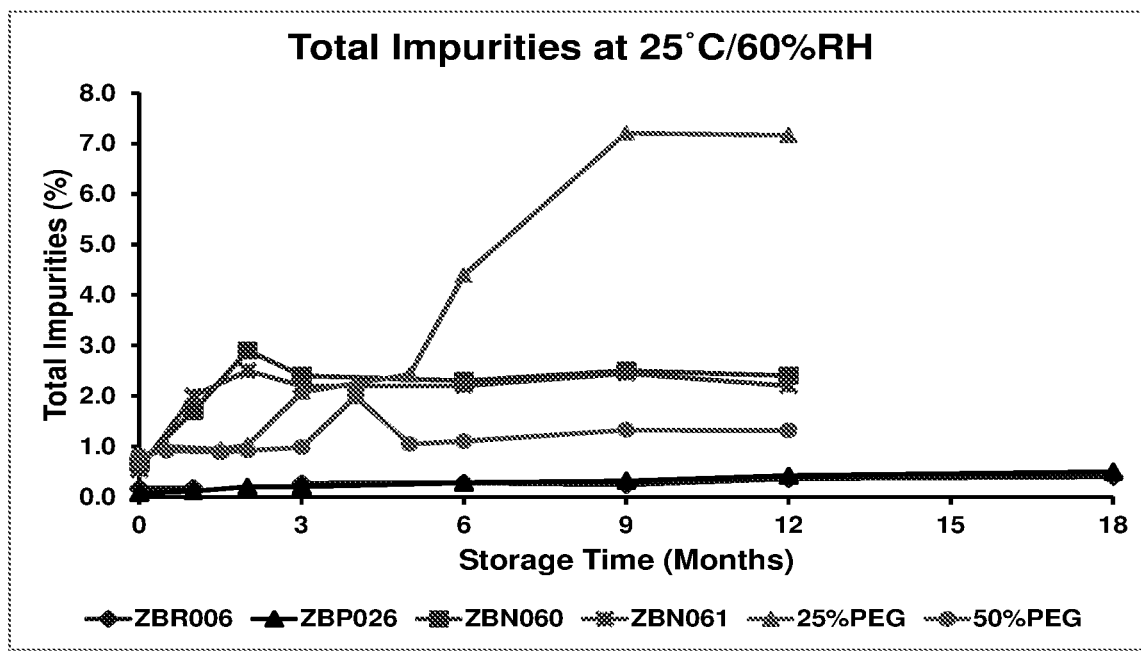
Figure 1. The total impurity (%) among different batches at 25°C/60%RH storage condition.

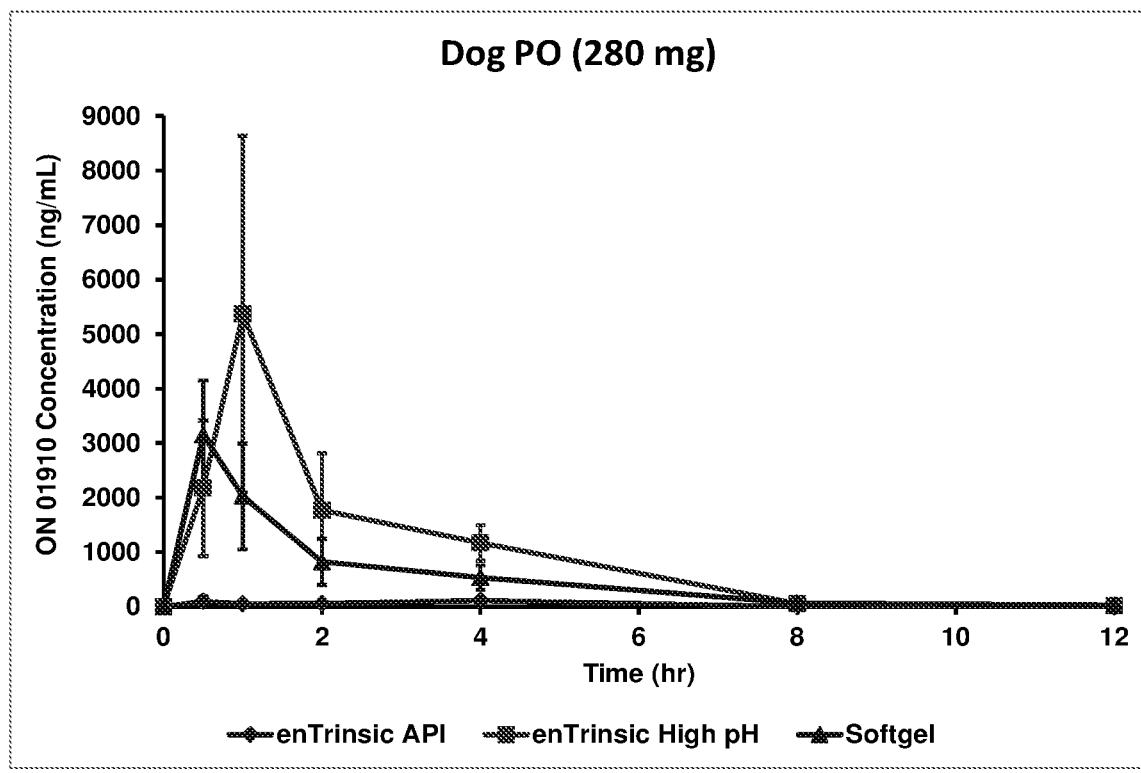
Figure 2. ON 01910 Concentration in dog plasma after oral doing with three different formulations understand# FORMULATION OF (E)-2,4,6-TRIMETHOXYSTYRYL-3-[(CARBOXYMETHYL)AMINO]-4-METHOXYBENZYLSULPHONE WITH ENHANCED STABILITY AND BIOAVAILABILITY

CROSS-REFERENCE TO RELATED APPLICATIONS

The present application is filed under 35 U.S.C. § 371 as the U.S. national phase of International Patent Application No. PCT/US2018/027514, filed Apr. 13, 2018, which designated the United States, and which claims the benefit of U.S. Provisional Application No. 62/485,355 filed Apr. 13, 2017; International Patent Application No. PCT/US2018/027514, filed Apr. 13, 2018, is a continuation-in-part of U.S. patent application Ser. No. 15/688,320, filed Aug. 28, 2017, which issued as U.S. Pat. No. 10,098,862 B2 on Oct. 16, 2018, and which claims the benefit of U.S. Provisional Application No. 62/485,355 filed Apr. 13, 2017; and International Patent Application No. PCT/US2018/027514, filed Apr. 13, 2018 is a continuation-in-part of International Application No. PCT/US2017/048890, filed Aug. 28, 2017, which claims the benefit of U.S. Provisional Application No. 62/485,355 filed Apr. 13, 2017; and all of these applications are hereby incorporated by reference in their entirety including all tables, figures, and claims.

FIELD OF THE INVENTION

The invention relates to pharmaceutical compositions of Rigosertib and their use for the treatment of cancer and proliferative disorders. Specifically, the compositions of the invention are formulations of Rigosertib that have good stability and bioavailability.

BACKGROUND OF THE INVENTION (E)-2,4,6-trimethoxystyryl-3-[(carboxymethyl)amino]-4-methoxybenzylsulphone and pharmaceutically acceptable salts thereof, is an antiproliferative agent that targets receptor tyrosine kinases and which arrest the Ras/Raf/MEK/ERK kinase cascade. The sodium salt is known as Rigosertib and ON 01910.Na and is described in U.S. Pat. No. 8,063,109 B2, U.S. Pat. No. 8,476,320 B2, and U.S. Pat. No. 7,598,232 B2.

Rigosertib is a drug candidate and has been formulated with water soluble polymers such as PEG 400, and with aqueous buffers, as described in U.S. Pat. No. 8,476,320 B2. However, these formulations lead to unacceptable levels of impurities. In particular, vials containing Rigosertib and PEG 400 show unacceptable levels of impurities in a matter of months when stored at room temperature and thus such vials must be stored under refrigeration, which is not convenient and adds expense. In addition, Rigosertib in 100% PEG 400, NF when administered via infusion bags can degrade over the course of long infusion periods reducing the ability to accurately deliver the drug. Also, vials containing Rigosertib, PEG 400, and phosphate buffer at high pH may form crystals. Thus, there is a need for pharmaceutical compositions with enhanced stability for oral and parenteral administration. There is also a need for pharmaceutical compositions with improved oral bioavailability.

When administered orally, a common adverse event is urothelial toxicity. Bowles, et al., *Clin. Cancer Res.* 2014 Mar. 15; 20(6): 1656-1665. Thus, there is also a need for a method of administering Rigosertib in a manner that reduces urothelial toxicity.

The present invention is predicated, at least in part, by the discovery that the Rigosertib solutions in polyethylene glycol solutions having an undiluted pH of about 11.0 to about 14.0 had surprisingly improved stability and impurity levels. These pharmaceutical compositions were also found to have surprisingly good oral bioavailability characteristics.

SUMMARY OF THE INVENTION

In a first aspect of the invention, there is provided pharmaceutical composition comprising
 a) (E)-2,4,6-trimethoxystyryl-3-[(carboxymethyl)amino]-4-methoxybenzylsulphone and pharmaceutically acceptable salts thereof;
 b) basic pre-treated low molecular weight polyethylene glycol;
 c) undiluted pH of about 11.0 to about 14.0; and
 d) less than 5% water or aqueous solution.

In a second aspect of the invention, there is provided pharmaceutical composition comprising
 a) (E)-2,4,6-trimethoxystyryl-3-[(carboxymethyl)amino]-4-methoxybenzylsulphone sodium salt;
 b) basic pre-treated PEG 400;
 c) undiluted pH of about 11.0 to about 14.0; and
 d) less than or equal to 2% water or aqueous solution.

In yet another aspect of the invention, there is provided a method of treating cancer and proliferative disorders by administering the pharmaceutical composition comprising
 a) (E)-2,4,6-trimethoxystyryl-3-[(carboxymethyl)amino]-4-methoxybenzylsulphone and pharmaceutically acceptable salts thereof,
 b) basic pre-treated low molecular weight polyethylene glycol;
 c) undiluted pH of about 11.0 to about 14.0; and
 d) less than 5% water or aqueous solution.

In yet another aspect of the invention, there is provided a method of treating cancer and proliferative disorders by administering the pharmaceutical composition comprising
 a) (E)-2,4,6-trimethoxystyryl-3-[(carboxymethyl)amino]-4-methoxybenzylsulphone sodium salt,
 b) basic pre-treated PEG 400;
 c) undiluted pH of about 11.0 to about 14.0; and
 d) less than or equal to 2% water or aqueous solution.

In yet another aspect of the invention, there is provided a pharmaceutical composition for use in treating cancer and proliferative disorders by administering the pharmaceutical composition comprising
 a) (E)-2,4,6-trimethoxystyryl-3-[(carboxymethyl)amino]-4-methoxybenzylsulphone and pharmaceutically acceptable salts thereof,
 b) basic pre-treated low molecular weight polyethylene glycol;
 c) undiluted pH of about 11.0 to about 14.0; and
 d) less than 5% water or aqueous solution.

In yet another aspect of the invention, there is provided a pharmaceutical composition for use in treating cancer and proliferative disorders by administering the pharmaceutical composition comprising
 a) (E)-2,4,6-trimethoxystyryl-3-[(carboxymethyl)amino]-4-methoxybenzylsulphone sodium salt,
 b) basic pre-treated PEG 400;
 c) undiluted pH of about 11.0 to about 14.0; and
 d) less than or equal to 2% water or aqueous solution.

In yet another aspect of the invention, there is provided an oral dosage regimen for the treatment of cancer and proliferative disorders with (E)-2,4,6-trimethoxystyryl-3-[(carboxymethyl)amino]-4-methoxybenzylsulphone sodium salt that reduces urotoxicity comprising administering (E)-2,4,6-trimethoxystyryl-3-[(carboxymethyl)amino]-4-methoxybenzylsulphone, and pharmaceutically acceptable salts thereof in a first dose of about 840 mg administered approximately 1-2 hours before breakfast, followed by a second dose of about 280 mg administered about 2 hours after lunch or about 6 to about 8 hours after the first dose. In yet another aspect of the invention, there is provided an oral dosage regimen for the treatment of cancer and proliferative disorders that reduces urotoxicity comprising administering (E)-2,4,6-trimethoxystyryl-3-[(carboxymethyl)amino]-4-methoxybenzylsulphone, and pharmaceutically acceptable salts thereof in a first dose of about 560 mg administered approximately 1-2 hours before breakfast, followed by a second dose of about 280 mg to 560 mg administered about 2 hours after lunch or about 6 to about 8 hours after the first dose.

In yet another aspect of the invention, there is provided the use of (E)-2,4,6-trimethoxystyryl-3-[(carboxymethyl)amino]-4-methoxybenzylsulphone sodium salt for the manufacture of a medicament for treating cancer and proliferative disorders, wherein the medicament is prepared to be administered according to the oral dosage regimen comprising a first dose of about 840 mg administered 1-2 hours before breakfast, followed by a second dose of about 280 mg administered about 2 hours after lunch or about 6 to about 8 hours after the first dose; or a first dose of about 560 mg administered 1-2 hours before breakfast, followed by a second dose of about 280 mg to 560 mg administered about 2 hours after lunch or about 6 to about 8 hours after the first dose.

All publications and patent applications mentioned in this specification are incorporated by reference in their entirety to the same extent as if each individual publication or patent application was specifically and individually indicated to be incorporated by reference.

BRIEF DESCRIPTION OF THE DRAWINGS

FIG. 1 shows percent of total impurities among formulations stored at 25° C./60% RH from 0 to 18 months.

FIG. 2 shows the ON 01910 concentration over time in dog plasma after dosing with three different ON 01910.Na oral capsules.

DETAILED DESCRIPTION OF THE INVENTION

The present invention provides novel pharmaceutical compositions that comprise (E)-2,4,6-trimethoxystyryl-3-[(carboxymethyl)amino]-4-methoxybenzylsulphone and pharmaceutically acceptable salts thereof. The pharmaceutical compositions are in the form of oral and parenteral solutions, especially liquid filled oral capsules and concentrated injectable solutions. The pharmaceutical compositions comprise basic low molecular weight polyethylene glycol, have an undiluted pH of about 11.0 to about 14.0; and less than 5% water or aqueous solution.

The novel pharmaceutical compositions of the invention have unexpectedly superior stability and significantly reduced impurities on storage compared to prior formulations as shown in Example 2. The pharmaceutical compositions of the invention also have very good oral bioavailability compared to prior formulations as shown in Examples 3-5.

In one embodiment, the sodium salt of (E)-2,4,6-trimethoxystyryl-3-[(carboxymethyl)amino]-4-methoxybenzylsulphone is used as the drug substance in the composition.

Low molecular weight liquid polyethylene glycols, for example, PEG 200, PEG 300, PEG 400, PEG 600, and PEG 800, are preferred water soluble polymers that can be used independently or in combination with each other, for example, in formulations of the present invention. Particularly preferred are PEG 200, PEG 300, PEG 400, and PEG 600. Lutrol® E 300, Lutrol® E 400 and Lutrol® E 600, for example, are commercially available from BASF Corporation, Mount Olive, N.J. PEG 400 (Polyethylene glycol 400, Macrogol 400, PEG 400, and Lutrol® E 400) is most preferred.

The basic low molecular weight polyethylene glycol is comprised of low molecular weight polyethylene glycol that has been treated with an alkalizing agent to raise the pH to about 10 to about 14, when measured using the direct probe method. In another aspect, the basic low molecular weight polyethylene glycol treated with alkalizing agent has a pH of about 11 to about 13 measured using the undiluted direct probe method. In another aspect, the pharmaceutical composition also comprises one or more alkalizing agents, which can be added after the (E)-2,4,6-trimethoxystyryl-3-[(carboxymethyl)amino]-4-methoxybenzylsulphone and pharmaceutically acceptable salts thereof is added to the basic low molecular weight polyethylene glycol.

In one aspect, the polyethylene glycol is pretreated with at least one base selected from the group consisting of barium hydroxide, sodium hydroxide, potassium hydroxide, sodium metasilicate, calcium hydroxide, trisodium phosphate, potassium carbonate, sodium carbonate, ammonium hydroxide, diethylamine, triethylamine, tromethamine, picoline, dicyclohexylamine, N,N'-dibenzylethylenediamine, and amino acids including arginine, lysine, and glycine, and their salts. In one aspect, the polyethylene glycol is pretreated with at least one base from the group comprising KOH and NaOH, particularly 4N to 10N, and more particularly 4N NaOH.

In one aspect, the pretreated PEG has a diluted pH of about 9.0 to about 11.0, or about 10.0 to about 11.0.

In one aspect, the pharmaceutical composition has a pH of about 12.0 to about 13.5 measured using the direct probe or undiluted method. In another aspect, the pharmaceutical composition has an undiluted pH of 12.6 to 13.0. In another aspect, the pharmaceutical composition has an undiluted pH of 12.8±0.2.

In one aspect, the pharmaceutical composition comprises less than or equal to 2.0% water or aqueous solution, or less than or equal to 1.0% water or aqueous solution. In another aspect, the composition is substantially free of added buffer.

In some embodiments, the pharmaceutical composition is suitable for parenteral administration and is from about 6 weight % to about 8.5 weight % (E)-2,4,6-trimethoxystyryl-3-[(carboxymethyl)amino]-4-methoxybenzylsulphone sodium salt. In some embodiments, the pharmaceutical composition is suitable for parenteral administration and is from 6.7 to 8.3% by weight (E)-2,4,6-trimethoxystyryl-3-[(carboxymethyl)amino]-4-methoxybenzylsulphone sodium salt. In some embodiments, the pharmaceutical composition is suitable for parenteral administration and is from about 6 to about 7% by weight (E)-2,4,6-trimethoxystyryl-3-[(carboxymethyl)amino]-4-methoxybenzylsulphone sodium salt. In some embodiments, the composition comprises about 87 to about 94 weight % PEG 400. In some embodiments, the composition comprises about 92 to about 94 weight % PEG 400. In some embodiments, the composition comprises about 6.7% by weight (E)-2,4,6-trimethoxystyryl-3-[(carboxymethyl)amino]-4-methoxybenzylsulphone sodium salt and about 92% by weight PEG 400.

When describing the % by weight of (E)-2,4,6-trimethoxystyryl-3-[(carboxymethyl)amino]-4-methoxybenzylsulphone sodium salt, it is the pure drug, not including water or impurities for example.

In some embodiments the pharmaceutical composition is suitable for oral administration and is from about 3 weight % to about 29 weight % (E)-2,4,6-trimethoxystyryl-3-[(carboxymethyl)amino]-4-methoxybenzylsulphone sodium salt. In some embodiments, the pharmaceutical composition is suitable for oral administration and is from 3.8 to 28.5% by weight (E)-2,4,6-trimethoxystyryl-3-[(carboxymethyl)amino]-4-methoxybenzylsulphone sodium salt. In some embodiments, the composition comprises about 64 to about 71 weight % PEG 400. In some embodiments, the composition comprises about 28.5% by weight (E)-2,4,6-trimethoxystyryl-3-[(carboxymethyl)amino]-4-methoxybenzylsulphone sodium salt and about 68.7% by weight PEG 400. In some embodiments, the composition comprises about 28.5% by weight (E)-2,4,6-trimethoxystyryl-3-[(carboxymethyl)amino]-4-methoxybenzylsulphone sodium salt, about 68.7% by weight PEG 400, and about 2.6% water. In some embodiments, the composition comprises about 28.5% by weight (E)-2,4,6-trimethoxystyryl-3-[(carboxymethyl)amino]-4-methoxybenzylsulphone sodium salt, about 70.5% by weight PEG 400, and less than about 1.0% water.

In some embodiments, the pharmaceutical composition is suitable for oral administration and has from about 35 mg/mL to about 300 mg/mL (E)-2,4,6-trimethoxystyryl-3-[(carboxymethyl)amino]-4-methoxybenzylsulphone sodium salt. In one aspect, the pharmaceutical composition is suitable for oral administration and is about 35 mg/mL, about 70 mg/mL, 140 mg/mL, or about 280 mg/mL (E)-2,4,6-trimethoxystyryl-3-[(carboxymethyl)amino]-4-methoxybenzylsulphone sodium salt.

In one aspect, the pharmaceutical composition is suitable for parenteral administration and is from about 6 to about 8.5 weight percent (E)-2,4,6-trimethoxystyryl-3-[(carboxymethyl)amino]-4-methoxybenzylsulphone sodium salt. In another aspect, the drug substance is about 75 mg/mL to about 280 mg/ml. In another aspect, the drug substance is about 75 mg/mL.

In one aspect, the pharmaceutical composition comprises about 92 weight % PEG 400 and about 6.7 weight % (E)-2,4,6-trimethoxystyryl-3-[(carboxymethyl)amino]-4-methoxybenzylsulphone, sodium salt.

In one aspect, the pharmaceutical composition is suitable for oral administration and is from about 35 mg/mL to about 300 mg/mL drug substance. In another aspect, the drug substance is about 35 mg/mL, about 70 mg/mL, 75 mg/mL, 140 mg/mL, or about 280 mg/mL.

In one aspect, the pharmaceutical composition comprises,
a) (E)-2,4,6-trimethoxystyryl-3-[(carboxymethyl)amino]-4-methoxybenzylsulphone, sodium salt;
b) basic pre-treated PEG 400;
c) undiluted pH of about 12.6 to about 13.0; and
d) less than or equal to 2% water or aqueous solution.

In one aspect of the invention, there is provided an oral dosage form comprising
a) about 35 to about 400 mg of (E)-2,4,6-trimethoxystyryl-3-[(carboxymethyl)amino]-4-methoxybenzylsulphone sodium salt,
b) basic pre-treated low molecular weight polyethylene glycol;
c) undiluted pH of about 11.0 to about 14.0; and
d) less than 5% water or aqueous solution.

In one embodiment, such oral dosage form is selected from a gel capsule, a non-gelatin capsule, and an enteric capsule. In one such oral dosage form, the concentration of the drug is about 35 to about 300 mg/mL, or about 35 to 280 mg/mL. In other embodiments, the dose of the drug is about 70 to 80 mg or about 270 to about 290 mg in the oral dosage form.

In one embodiment, the disease treated is a hematological cancer or proliferative disorder. In one embodiment, the disease is selected from AML and MDS.

Terms

Unless defined otherwise, all technical and scientific terms used herein have the same meaning as is commonly understood by one of skill in the art to which the invention(s) belong.

The terms used in the specification have the following meanings:

As used herein, the term "alkalizing agent" refers to bases such as barium hydroxide, sodium hydroxide, potassium hydroxide, sodium metasilicate, calcium hydroxide, trisodium phosphate, potassium carbonate, sodium carbonate, ammonium hydroxide, diethylamine, triethylamine, tromethamine, picoline, dicyclohexylamine, N,N'-dibenzylethylenediamine, and amino acids including arginine, lysine, and glycine, and their salts. Preferred alkalizing agents are KOH and NaOH, particularly 4N to 10N, and more particularly 4N NaOH.

As used herein, the term "basic low molecular weight polyethylene glycol" refers to low molecular weight polyethylene glycol that has been treated with one or more alkalizing agents such that it has an undiluted pH of about 11 to about 13, or a pH of about 9 to about 11 measured according to the monograph for PEG described in the second supplement to USP39-NF34, pp 8560-8563, Dec. 1, 2016. The detailed procedure of measuring pH is provided in Example 1 below.

As used herein, the term "chemical purity" refers to the percentage of impurities present in the product. Impurities may be in the form of, for example, the presence of unwanted solvents, degradation products or oxidation products. In particular embodiments the chemical purity is high, that is above 95%, especially greater than 97%, 98%, or 99%.

The term "substantially free of added buffer" refers to a pharmaceutical composition having less than 1% by weight of an added buffer. The added buffer could be either in the solid form or as an aqueous solution where it would be made up of a weak acid and its conjugate base.

As used herein, the meaning of the term "about" depends upon the context in which it is used. When used with respect to pH, the term "about" includes levels within ±0.2 pH units. When used with respect to drug concentration, the term "about" includes concentrations of ±5% in parenteral compositions, and includes concentrations of ±15% in solutions for oral administration. For example, about 75 mg/mL Rigosertib parenteral composition includes 67.5 to 82.5 mg/mL Rigosertib.

As used herein, the term "pharmaceutical composition" means, for example a mixture containing a specified amount of a therapeutic compound, e.g. a therapeutically effective amount, in a pharmaceutically acceptable carrier to be administered to a mammal, e.g. a human in order to treat a disease.

As used herein, the term "pharmaceutically acceptable" refers to those compounds, materials, compositions and/or dosage forms, which are, within the scope of sound medical judgment, suitable for contact with the tissues of mammals, especially humans, without excessive toxicity, irritation, allergic response and other problematic complications commensurate with a reasonable benefit/risk ratio.

The term "treatment" is understood to mean the management and care of a patient for the purpose of combating a disease, condition, or disorder.

The term "low molecular weight polyethylene glycol," or "PEG," is understood to include PEG 200, PEG 300, PEG 400, PEG 600, and PEG 800, and combinations thereof.

Dosage Forms

Pharmaceutical compositions include those suitable for oral or parenteral (particularly intravenous) administration. The pharmaceutical compositions can be placed in unit dosages thereof, and in such form may be employed as liquids such as solutions, elixirs, or capsules filled with the same, all for oral use, or in the form of sterile injectable solutions for parenteral use including concentrated solutions that are diluted prior to administration. Such pharmaceutical compositions and unit dosage forms thereof may comprise conventional ingredients in conventional proportions, and such unit dosage forms may contain any suitable effective amount of the active ingredient commensurate with the intended daily dosage range to be employed.

Rigosertib can be administered in a wide variety of oral and parenteral dosage forms. Oral dosage forms include a concentrated liquid in a hard or soft capsule. The shell of the capsule may be composed of gelatin or non-gelatin. The capsule may be coated with a delayed release polymer or such delayed release polymer may be part of the composition of the shell. In a particular embodiment, Rigosertib is formulated as a liquid in a soft gel capsule for oral administration. In another embodiment, Rigosertib is formulated as a liquid in enteric coated capsules. In another embodiment, Rigosertib is formulated as a liquid in a capsule made of delayed release cellulosic material, such as the enTRinsic™ capsule by Capsugel corporation.

Rigosertib can also be administered orally by mixing the concentrated liquid formulation in water or other suitable beverage and then having the patient drink the liquid.

Aqueous solutions suitable for oral use can be prepared by dissolving the active compound in polyethylene glycol and adding suitable colorants, flavors, stabilizing and thickening agents, as desired. Oral formulations can include standard carriers. Such compositions contain a therapeutically effective amount of the compound, preferably in purified form, together with a suitable amount of carrier so as to provide the form for proper administration to the patient.

Oral formulations containing 35 milligrams, 70 milligrams, 140 milligrams, 280 milligrams, 300 milligrams, or 400 milligrams of active ingredient or, more broadly, 35 to 400 milligrams, per capsule, are accordingly suitable representative unit dosage form. Such oral dosage forms may have a concentration of Rigosertib of about 35 mg/mL to about 300 mg/mL. Such oral dosage forms may contain a dose of 35 mg, 70 mg, 75 mg, 140 mg or 280 mg.

The active agent may be formulated for parenteral administration (e.g., by injection, for example via continuous infusion after dilution of the concentrated formulation) and may be presented in unit dose form in ampoules, vials, pre-filled syringes, small volume infusion or in multi-dose containers with or without an added preservative. Parenteral formulations may include suitable anti-oxidants, osmolality adjusting agents, stabilizing agents, and other pharmaceutically acceptable excipients. Suitable anti-oxidants include sodium bisulfite, sodium sulfite, sodium ascorbate, L-cysteine and sodium thiosulfate, sodium formaldehyde sulfoxylate, citric acid, d,l-α-tocopherol, butylated hydroxy anisole, butylated hydroxy toluene, monothioglycerol, ascorbic acid, and propyl gallate.

In a particular embodiment, solutions in vials contain about 6% to about 8.5% by weight of Rigosertib. In another embodiment, solutions in vials contain about 6% to about 7% by weight of Rigosertib. These vials may be used for parenteral solutions or oral solutions mixed to form a beverage.

In a preferred embodiment, the composition of the invention is formulated in accordance with routine procedures as a pharmaceutical composition adapted for intravenous administration to human beings. Typically, compositions for intravenous administration are sterile solutions in basic polyethylene glycol. Where necessary, the composition may also include a solubilizing agent and a local anesthetic such as lignocaine to ease pain at the site of the injection. Generally, the ingredients are supplied either separately or mixed together in unit dosage form, for example, as a water free concentrate in a hermetically sealed container such as a vial, an ampoule or sachette indicating the quantity of active agent. Where the composition of the invention is to be administered by infusion, it can be dispensed with an infusion bag or bottle containing fluid suitable for dilution and/or administration such as sterile pharmaceutical grade water, ringers solution, lactated ringers solution, 5% dextrose solution, or saline. The infusion period can be from about 15 minutes to about 7 days. Where the composition of the invention is administered by injection, an ampoule of sterile water for injection or saline can be provided so that the ingredients may be mixed prior to administration.

Parenteral formulations may contain concentrations of Rigosertib of about 35 mg/mL to about 300 mg/mL. In some embodiments, the concentration of Rigosertib is about 75 mg/mL.

The pharmaceutical compositions of the invention have been presented in unit-dose or multi-dose containers, for example, sealed ampoules and vials, only the addition of the sterile liquid carrier, for example, water for injections, is needed immediately prior to use.

The present inventions includes kits comprising vials or ampoules of Rigosertib and a container of a suitable liquid as carrier, such as water.

Methods of Treatment

Malignant and metastatic conditions which can be treated with the therapeutic method of the invention include, but are not limited to, hematological cancers and solid tumors, including all cancers described herein and otherwise known in the art (for a review of such disorders, see Fishman et al., Medicine, 2d Ed., J. B. Lippincott Co., Philadelphia (1985)).

Hematological malignancies are the type of cancers that affect blood, bone marrow, and lymph nodes. As the three lineages are intimately connected through the immune system, a disease affecting one of the three lineages will often affect the other lineages. For example, although lymphoma is a disease of the lymph nodes, it often spreads to the bone marrow, affecting the blood and occasionally producing a paraprotein.

Hematological cancers usually derive from either of the two major blood cell lineages: myeloid and lymphoid cell lines. The myeloid cell line normally produces granulocytes, erythrocytes, thrombocytes, macrophages and mast cells; the lymphoid cell line produces B, T, NK and plasma cells. Lymphomas, lymphocytic leukemias, and myeloma are from the lymphoid line, while acute and chronic myelogenous leukemia, myelodysplastic syndromes and myeloproliferative diseases are myeloid in origin. Examples of hematological diseases include, but are not limited to, Leukemias, acute lymphoblastic leukemia (ALL), acute myelogenous leukemia (AML), MDS (Myelodysplastic Syndrome), MPN (Myeloproliferative neoplasm), MDS/MPN overlap, and PDGFR/FGFR1-rearranged myeloid/lymphoid neoplasms with eosinophilia, chronic lymphocytic leukemia (CLL), small lymphocytic lymphoma (SLL), chronic myelogenous leukemia (CML), acute monocytic leukemia (AMOL), lymphomas, Hodgkin's lymphomas (all four subtypes), and non-Hodgkin's lymphomas, among others.

Examples of solid tumors include cancer of prostate, lung, breast, ovarian, stomach, pancreas, larynx, esophagus, testes, liver, parotid, biliary tract, colon, rectum, cervix, uterus, endometrium, kidney, bladder, thyroid cancer; primary tumors and metastases, melanomas; glioblastoma, Kaposi's sarcoma; leiomyosarcoma, non-small cell lung cancer, colorectal cancer, head and neck, among others.

The pharmaceutical compositions and methods of the invention are particularly effective in treating and/or ameliorating symptoms of diseases related to hematopoietic stem cells. The cellular elements of blood originate from the pluripotent hematopoietic stem cell. Stem cells have extensive regenerative and differentiating capacity and generate lymphoid and myeloid precursors, which then produce lymphocytes, neutrophils, eosinophils, basophils, erythrocytes, and platelets. In myelodysplastic syndrome, a dysregulation in the differentiation process appears to occur. Mortality in myelodysplastic syndrome is related to bleeding, recurrent infection, and leukemic transformation. In the absence of treatment, myelodysplastic syndrome can be a rapidly fatal disease, with or without the transformation to acute myeloid leukemia. An estimated 20-40% of adults with myelodysplastic syndrome develop leukemia, and 30-40% of myelodysplastic syndrome patients succumb to infection, bleeding, or both.

Acute myeloid leukemia is the most common variant of acute leukemia occurring in adults, comprising approximately 80-85% of cases of acute leukemia diagnosed in individuals greater than 20 years of age. The heterogeneous group of acute leukemic disorders of myeloid hematopoietic cells has been called a variety of names including acute myelogenous leukemia, acute myelocytic leukemia, acute myeloid leukemia, acute myeloblastic leukemia, acute granulocytic leukemia, and acute nonlymphocytic leukemia. The myeloid character of the reddynant blasts can be determined by detection of characteristic morphologic and immunologic findings. Clinical aspects of the disease are reviewed by C. A. Schiffer and R. M. Stone in Cancer Medicine, Ed. David W. Kufe et al., 6.sup.th Edition, B. C. Decker, 2003, the entire disclosure of which is incorporated herein by reference.

Due to the dual effect on tumor cell survival and mitotic pathways, Rigosertib has potential utility in a variety of cancer types, including hematological malignancies and solid tumors. Ongoing clinical trials are evaluating the activity of Rigosertib in MDS: Phase III and Phase II trials, other blood malignancies including AML and CLL: Phase I trials, solid tumors, including randomized Phase II in metastatic pancreatic cancer and Phase II in ovarian cancer.

Extensive Phase I, Phase II and Phase III studies with Rigosertib have been or are being conducted at leading institutions in the U.S. and abroad in more than 1200 patients with solid tumors and hematological cancers, including MDS and AML. MDS and AML are blood disorders widely recognized as difficult to manage, with limited therapeutic options available for patients, especially those with drug-resistant disease.

Rigosertib has been safe and active in MDS and AML patients treated in Phase I and Phase II clinical trials designed to determine the optimal dose and anti-leukemia efficacy of this drug. These studies are a part of comprehensive evaluation of the safety and activity of Rigosertib. To date, more than 400 patients with MDS or AML have been treated in phase I and Phase II trials. These studies have led to an ongoing multi-site Phase III pivotal trial in higher risk MDS patients who have failed prior treatment with hypomethylating agents.

According to one embodiment, Rigosertib was given as an intravenous infusion to MDS patients. In one trial, patients received 800 mg Rigosertib for two to five days every other week. According to another embodiment, patients received 650 to 1,700 mg Rigosertib for three to six days every other week. According to yet another embodiment, patients were initially treated with 800 mg to 1,500 mg Rigosertib for two days every week for three weeks followed by one week without treatment. The treatment schedule in these studies was later changed to 1,800 mg Rigosertib per day for three days every other week. In general, patients showed at least a 50 percent decrease or stabilization in the number of immature bone marrow cells (blasts).

According to one embodiment, Rigosertib is given in an intravenous infusion to cancer patients with 650 mg to 3,120 mg per day.

According to one embodiment, Rigosertib was given orally to MDS patients. In one trial, 70 mg, 140 mg, 280 mg, 560 mg, and 700 mg was administered once a day for one week, and in another trial Rigosertib was administered 70 mg BID, 140 mg BID, 280 mg BID, 560 mg BID, 700 mg BID, or a total of 1120 mg per day in divided doses for the first 14 days of a 21 day cycle.

According to one embodiment, Rigosertib was given orally to MDS patients in a bifurcated dose schedule. In one trial, 560 mg was administered in the morning and 280 mg as a second dose in the evening for two weeks followed by one week off of Rigosertib. Rigosertib when administered orally, is typically administered in the fasting state, particularly about 1 to about 2 hours before or after a meal, and more particularly about 2 hour before or after a meal.

According to one embodiment, Rigosertib is given orally to cancer patients in a dose regimen intended to reduce urothelial toxicity comprising administering 560 mg approximately 1 to 2 hours before breakfast, followed by 560 mg or 280 mg administered about 2 hours after lunch or about 6 to about 8 hours after the first dose; or comprising administering 840 mg approximately 1 to 2 hours before breakfast, followed by 280 mg administered about 2 hours after lunch or about 6 to about 8 hours after the first dose. According to modelling, by administering the second dose at a shorter interval, bladder concentration of Rigosertib and its metabolites will be reduced during the sleep cycle and thereby reduce urothelial toxicity. In one embodiment, the Rigosertib is administered for three weeks followed by one week off. In one embodiment, Rigosertib is given orally to cancer patients in a dose regimen intended to reduce urothelial toxicity comprising administering 560 mg approximately 1 to 2 hours before breakfast, followed by 560 mg or 280 mg administered about 2 hours after lunch or about 6 to about 8 hours after the first dose; or comprising administering 840 mg approximately 1 to 2 hours before breakfast, followed by 280 mg administered about 2 hours after lunch or about 6 to about 8 hours after the first dose, wherein the Rigosertib is administered for three weeks followed by one week off, and said patient is treated with injectable azacitidine 75 mg/m$^2$/day for one week per month starting on day 8 of a 28 day cycle. In one such embodiment, said cancer patient has hematological cancer. In one such embodiment said hematological cancer is selected from MDS and AML. In one embodiment, said patient is encouraged to drink at least 2 L of fluid per day. In one embodiment, said patient is recommended to take sodium bicarbonate (650 mg) three times per day, particularly if the urine pH is less than 7.5.

In one embodiment, Rigosertib is given orally in the fasting state to hematological cancer patients in a dose regimen intended to reduce urothelial toxicity comprising administering 560 mg approximately 1 to 2 hours before breakfast, followed by 560 mg or 280 mg administered about 2 hours after lunch or about 6 to about 8 hours after the first dose; or comprising administering 840 mg approximately 1 to 2 hours before breakfast, followed by 280 mg administered about 2 hours after lunch or about 6 to about 8 hours after the first dose, wherein the Rigosertib is administered for three weeks followed by one week off, and said patient is treated with injectable azacitidine 75 mg/m$^2$/day for one week per month starting on day 8 of a 28 day cycle. In one such embodiment, said hematological cancer patient has cancer selected from MDS and AML. In one embodiment, said patient is encouraged to drink at least 2 L of fluid per day. In one embodiment, said patient is recommended to take sodium bicarbonate (650 mg) three times per day, particularly if the urine pH is less than 7.5.

It is intended herein that by recitation of such specified ranges, the ranges recited also include all those specific integer amounts between the recited ranges. For example, the range of about 650 mg to 1,700 mg Rigosertib or 800 mg to 1,500 mg Rigosertib, it is intended to also encompass 600 mg, 750 mg, 850 mg, 900 mg, 950 mg, 1000 mg, 1100 mg, 1200 mg, 1300 mg, 1400 mg, 1600 mg, and 1700 mg Rigosertib.

In another embodiment, the efficacy of Rigosertib was shown in higher risk MDS patients who had previously failed treatment with Vidaza (azacitidine) or Dacogen (decitabine). They found that previous treatment failure did not have a negative impact on response to Rigosertib. These patients experienced at least a 50 percent decrease or stabilization in the number of immature bone marrow cells, and their median survival was about 36 weeks.

Acquired Resistance Cancers

According to one embodiment of the invention, the compound of the invention can be administered to drug resistant cancer patients, prior to, concomitant with, and/or subsequent to the administration of the specific anticancer agent to which the cancer patient has acquired resistance.

Examples of anticancer agents include, cytotoxic agents, chemotherapeutic agents (including alkylating agents, antimetabolites, anthracyclines, alkaloids, topoisomerase inhibitors, monoclonal antibodies, among others), erythropoiesis modulating agents comprising ESAs including EPO (endogenous, recombinant and/or synthetic EPO), epoetin alfa, Procrit, Epogen, epoetin beta, darbepoetin alfa, and/or methoxy polyethylene glycol-epoetin beta; DNA methyltransferase inhibitors (including azacitidine, decitabine, 5-fluoro-2'-deoxycitidine, 5,6-dihydro-5-azacytidine, zebularine, fazarabine, hydralizine, procaine, procainamide, epigallocatechin gallate, psammaplin A, or (S)-2-(1,3-fioxo-1, 3-dihydro-isoindol-2-yl)-3-(1H-indol-3-yl)-propionic acid, or a pharmaceutically acceptable salt thereof), immunomodulators such as lenalidomide, among others.

Failure of a patient's cancer to respond to a specific therapy can result from one of two general causes: host factors and specific genetic or epigenetic alterations in the cancer cells. Host factors include poor absorption or rapid metabolism or excretion of a drug, resulting in low serum levels; poor tolerance to effects of a drug, especially in elderly patients, resulting in a need to reduce doses below optimal levels; inability to deliver a drug to the site of a tumor, as could occur with bulky tumors or with biological agents of high molecular weight and low tissue penetration such as monoclonal antibodies and immunotoxins. In addition, various alterations in the host-tumor environment can affect the response of the tumor to cancer therapy, these effects include local metabolism of a drug by normal cells, abnormal and/or unusual features of the tumor blood supply that may affect transit time of drugs within tumors, among others.

The pharmaceutical composition of the invention and the therapeutic regimen as claimed are effective to overcome one or more of the aforementioned obstacles in cancer therapy by raising the tolerance or resistance to anticancer agents or therapies. Accordingly, the method of the invention provides additional tools for effective cancer therapy to combat and defeat drug resistance in cancer patients.

Multidrug resistance, the principal mechanism by which many cancers develop resistance to chemotherapy drugs, is a major factor in the failure of many forms of chemotherapy. It affects patients with a variety of blood cancers and solid tumors. Tumors usually consist of mixed populations of malignant cells, some of which are drug-sensitive while others are drug-resistant. Chemotherapy can destroy drug-sensitive cells, but leaves behind a higher proportion of drug-resistant cells. As the tumor begins to grow again, chemotherapy may fail because the remaining tumor cells are now drug resistant.

Resistance to therapy has been correlated to the presence of at least two molecular "pumps" in tumor-cell membranes that actively expel chemotherapy drugs from the interior. This allows tumor cells to avoid the toxic effects of the drug or molecular processes within the nucleus or the cytoplasm. The two pumps commonly found to confer chemo-resistance in cancer are P-glycoprotein and the so-called multidrug resistance—associated protein (MRP). Because of their function and importance, they are the targets of several anticancer efforts.

According to one embodiment, the compositions and methods of the invention overcome resistance to DNA methyltransferase inhibitors, ESAs, or a combination thereof.

The methods and compositions of the invention are useful in treatment of cancer and the anemia associated with cancer, specifically in patients who have acquired resistance to exogenous erythropoietin (EPO). Resistance to exogenous EPO is associated with an increased risk of death. Anemia in cancer patients rises through many different mechanism of actions and pathways, it can be the direct effects of the cancer cells in the body, as a result of biologically active products of the cancer cells, or as a consequence of the treatment of cancer. There is also an association between anemia and progression of blood cancers. The main causes of anemia are deficient production of erythropoietin (EPO), iron deficiency, and a chronic disease with endogenous EPO resistance. Up to 10% of patients receiving EPO are hyporesponsive to therapy and require large doses of the agent. Proinflammatory cytokines antagonize the action of EPO by exerting an inhibitory effect on erythroid progenitor cells and by disrupting iron metabolism. See, U.S. Pat. No. 8,664,272 B2.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

This invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES (E)-2,4,6-Trimethoxystyryl-[(3-carboxymethyl)amino-4-methoxybenzylsulphone sodium salt (ON 01910.Na) was synthesized as described in Example 4a in U.S. Pat. No. 7,598,232. However, other pharmaceutically suitable methods can be used. The (E)-2,4,6-Trimethoxystyryl-[(3-carboxymethyl)amino-4-methoxybenzylsulphone sodium salt may contain 0.1% to 3% water.

PEG 400 was obtained from Croda and may contain 0.1 to 2% water. It has a density of 1.13 Gms/mL.

Example 1

Measurement of pH by Dilution Method and Direct Probe Method
Dilution Method

Dissolve 5 g of sample in 100 mL of carbon dioxide free water and add 0.30 mL of saturated potassium chloride solution. The detailed sample preparation technique is described in Second Supplement to USP 39-NF34; pg 8562. Measure the pH of the resulting solution at 25° C.±2° C. as described in USP 39 <791>.

2.1 Measurement of pH by Direct Probe Method, Also Called Undiluted pH

The Solvotrode Probe (Metrohm, Cat #: 6.0339.010 or equivalent) is designed to measure the pH of non-aqueous solutions, which generally refers to solutions have ≤2.0% water. The new probe is first inspected, conditioned and tested before use following manufacturer's instructions. Then calibration is performed on the pH meter with Solvotrode electrode by use of pH standard buffer solutions of pH 4, 7, 9 and 12. The pH of a pH 13 buffer solution (0.2 M KCl adjusted to pH to 13 by 0.2 M NaOH) was checked as a bracketing standard. The valid range of the method is pH 9.1 to 13.0. After calibration, switch to "Measure" mode on the pH meter; Rinse the electrode with distilled water and wipe off the water from the bulb using soft tissue. Take the drug product solution and allow the sample to reach room temperature. Obtain and record the temperature of the sample (should be within 25° C.±3° C.). Then pour a minimum of 15 mL sample into a clean 20 mL beaker or cup. Drop a small stirring bar into the beaker. Place the sample on a stirring plate and start stirring. Submerge the bulb of the electrode into the sample and start the timer. Record the pH value in 3 decimal places at 10 min. Clean and rinse the electrode with DI water thoroughly. Hydrate the electrode and measure the pH one more time using the same sample. After completion of all sample analysis, verify reading of pH13 buffer solution as bracketing solution. Calculate and report the mean pH value in 2 decimal places. This method is used to determine the undiluted pH of the formulation. The undiluted pH is typically about 2 pH units higher than a corresponding sample measured using Dilution Method.

Example 2

Manufacture and Long Term Stability of non-pH adjusted and pH-adjusted drug product for Rigosertib (ON 01910.Na) Injection
Introduction Rigosertib (ON 01910.Na) Injection (75 mg/mL) was manufactured initially without pH adjustment. The drug product formulation is a non-aqueous solution of Rigosertib in PEG 400. The stability of the drug product was significantly improved by increasing the drug product pH by addition of NaOH. The manufacturing process and stability were compared between the non-pH adjusted drug products (ZBN060 & ZBN061) and pH adjusted drug products (ZBP026 & ZBR006). Also provided is data on aqueous solutions of Rigosertib in 25% PEG 400/75% phosphate buffer, pH 10.0 and 50% PEG 400/50% phosphate buffer, pH 10.0 as shown in Examples VIII and IX of U.S. Pat. No. 8,476,320 B1.

Manufacture Process

ON 01910.Na non-pH adjusted concentrate was prepared by adding small amounts of ON 01910.Na API slowly to PEG 400. The contents were mixed until completely dissolved. Then the solution was filtered before filling into vials, stoppering and sealing.

For the pH adjusted concentrate, the PEG 400 was pretreated with 4.0 N NaOH to increase the undiluted pH to about pH 10 to about pH 11. Then compounding was started by adding ON 01910.Na API slowly with stirring into the NaOH treated PEG 400. After stirring for 2 hours, the pH of the mixture was measured by the direct probe method and if the pH was not within the target (12.8±0.2), additional 4.0 N NaOH was added in ~250 µl increments into the mixture. Stirring was continued for another 30-40 minutes before the next pH measurement until the final pH reached the target pH (12.6±0.2). The final composition of ZBR006 contained 0.8% water and the final water content of ZBP026 is calculated to be 0.9% by weight. Then the drug product solution was filtered before vial filling, stoppering and sealing. The total amounts of the ingredients for the two lots of high pH formulation according to the present invention is provided in Table 1.

TABLE 1

Composition of High pH Formulation of Rigosertib

| Ingredients | ZBP026 | ZBR006 |
| --- | --- | --- |
| ON 01910. Na | 2.625 Kgs | 3.75 Kgs |
| PEG 400 | 37.342 Kgs | 54.06 Kgs |
| 4N Sodium Hydroxide Solution | 110 ml | 205 ml |

Stability

The drug product vials were put into stability chambers at different conditions and the samples were pulled out for analysis at different time points according to stability protocols. The total impurity at 25° C./60% RH storage condition for the above four batches as well as the 25% and 50% aqueous PEG/buffer formulations of Examples VIII and IX of U.S. Pat. No. 8,476,320 are summarized in Table 2. The total impurity amongst different batches is also plotted in FIG. 1.

TABLE 2

Summary of total impurity at 25° C./60% RH condition.

| DP Batch # | ZBR006 | ZBP026 | ZBN060 | ZBN061 | 25% PEG | 50% PEG |
|---|---|---|---|---|---|---|
| API Batch # | 14208342 | ONA1NA05J | ONA1NA03J | ONA1NA04J | NA | NA |
| Vial Fill (mL) | 24 | 8 | 24 | 24 | NA | NA |
| Initial pH | 12.71* | 12.65* | 9.11* | 9.02* | 10.97** | 10.68** |
| Time (M) | | | Total Impurity (%) | | | |
| 0 | 0.17 | 0.07 | 0.66 | 0.54 | 0.72 | 0.83 |
| 0.5 | NA | NA | NA | NA | 1.00 | 0.91 |
| 1 | 0.18 | 0.11 | 1.7 | 2 | 0.94 | 0.88 |
| 1.5 | NA | NA | NA | NA | 1.03 | 0.92 |
| 2 | NA | 0.20 | 2.9 | 2.5 | 2.07 | 0.98 |
| 3 | 0.27 | 0.20 | 2.4 | 2.2 | 2.25 | 1.99 |
| 4 | NA | NA | NA | NA | 2.43 | 1.04 |
| 5 | NA | NA | NA | NA | 4.39 | 1.10 |
| 6 | 0.28 | 0.28 | 2.3 | 2.2 | 7.21 | 1.33 |
| 9 | 0.24 | 0.32 | 2.5 | 2.45 | 7.16 | 1.32 |
| 12 | 0.36 | 0.42 | 2.4 | 2.2 | 6.57 | 1.33 |
| 18 | 0.40 | 0.50 | NA | NA | NA | NA |

NA: not available.
*Direct probe, undiluted pH method used
**pH measured using standard probe for aqueous solutions without additional dilution of sample; USP 39 <791>

SUMMARY

The total impurity for the non-pH adjusted drug product (ZBN060 & ZBN061) was out of the specification limit (2.0%) when stored at 25° C./60% RH for 2 months and longer. The 25% PEG with phosphate buffer was also out of specification when stored at 25° C./60% RH for 2 months and longer. In contrast, the total impurity was greatly reduced at release for the pH-adjusted drug product (ZBR006 & ZBP026) and the increase was also slowed down significantly in the same storage condition (25° C./60% RH). The total impurity was not more than 0.5% even after 18 months storage at 25° C./60% RH, whereas the total impurity for the other formulations was over 1.3% at 12 months. The total impurity of the pH-adjusted drug product (ZBR006 & ZBP026) would be expected to be within the specification (NMT2.0%) at 25° C./60% RH for 24 months based on the trend.

Example 3

Oral Absorption of Rigosertib in Dogs after Dosing with Rigosertib Solution
Introduction Rigorsertib (ON 01910.Na) oral solutions were dosed to fasted non-naïve male beagle dogs and the absorptions was compared amongst two formulations.
1. Experimental Procedure Two formulation of oral Rigosertib solutions were prepared:
A. ON 01910.Na 75 mg/mL regular pH concentrate (final pH by USP <791>: 7.11)
B. ON 01910.Na 75 mg/mL high pH concentrate (final pH by USP <791>: 10.12)

2.1. Preparation of Drug Product Formulation

ON 01910.Na non-pH adjusted concentrate was prepared by adding ON 01910.Na API slowly into PEG 400 and stirred using overhead stirring until a homogenous solution was obtained. The drug product was then filtered through a 0.45 μm membrane filter. The pH of final drug product was measured dilution method (final pH is 7.11) and then stored at refrigerated condition. The high pH formulation was prepared by adding 4.0 N NaOH into PEG 400 vehicle first and then adding weighed amount of ON 01910.Na API slowly and mixing for ~2 hrs until a homogenous solution was obtained. The pH of the solution was measured and further adjusted with 4.0 NaOH until pH close to 10 was achieved. The drug product was then filtered through a membrane filter and the final pH was measured by dilution method. The drug product was then filtered through 0.45 μm membrane filter and stored under refrigerated condition before use. The final pH is 10.12. The final concentration of both the formulations were ~75 mg/ml.

2.2. Animal Dosing and Blood Collection

All animals were fasted for at least 12 hours before single oral administration at 25 mg/kg via oral gavage. Approximately 1.0 mL whole blood was collected into a tube containing $K_2$EDTA via jugular vein. At pre-dose, approximately 10 mL whole blood was collected. Approximately 30 minutes post collection, the blood was gently mixed to assure distribution of the anti-coagulant. Immediately after the blood sample has been collected and mixed it was placed on wet ice or refrigerated and then centrifuged at 4-8° C. for 10 minutes at approximately 3,000 rpm. Plasma was then harvested and stored frozen at approximately −80° C. within two hours from sample collection. Detailed study design is described below (Table 3).

TABLE 3

Study Design

| Group # | Animal # | Test article | Dosage Level (mg) | Dose Route | Dosing Schedule | Blood Collection Times (hr) |
|---|---|---|---|---|---|---|
| 1 | 3 | ON01910.Na 75 mg/mL Non-adjusted pH (A) | 25 mg/kg | PO | Once, Day 1 | Predose*, 0.5, 1, 2, 4, 8, 12 and 24 hr |

TABLE 3-continued

Study Design

| Group # | Animal # | Test article | Dosage Level (mg) | Dose Route | Dosing Schedule | Blood Collection Times (hr) |
|---|---|---|---|---|---|---|
| 96-Hour Washout Period | | | | | | |
| 2* | 3 | ON01910.Na 75 mg/mL High pH (B) | 25 mg/kg | PO | Once, Day 5 | Predose*, 0.5 1, 2, 4, 8, 12 and 24 hr |

*The same animals from group 1 were dosed for group 2

2.3. Drug Concentration Determination by LC-MS/MS Method

The drug concentration in dog plasma samples was determined through multiple reaction monitoring (MRM) by an in-house developed LC-MS/MS assay with calibration range of 10-4000 ng/mL for ON 01910. Briefly, samples were extracted by protein precipitation method using five volumes of acetonitrile. After vortex the samples were centrifuged at 12,000 rpm for 5 minutes at refrigerated condition. The supernatant was then collected and 5 µL was injected into Agilent 6410 LC/MS/MS system for analysis. The mobile phase A (MPA) is 10 mM ammonium acetate in water and the mobile phase B (MPB) is 0.1% formic acid in acetonitrile. The samples were separated by isocratic elution with 50% MPB for 5.5 min on Hypersil BDS C18 column (5 µm, 100×2.1 mm). The flow rate used was 0.25 mL/min.

2. Results

The concentrations of ON 01910 after dosing with two different ON 01910.Na drug product solutions are summarized in Table 4, which provides the data of individual dogs identified as A1, A2, and A3, where the same dog was first administered the non-adjusted pH formulation and then the high pH formulation with a washout period of 96 hours between the dosing. The absorption and exposure of drug is significantly higher in dogs dosed orally with high pH formulation compared to regular pH formulation.

Dog Data

TABLE 4

Oral Absorption of Rigosertib in Individual Dog -Dose - 25 mg/kg

| Formulation | Animal Number | Cmax (ng/ml) | AUC (ng-hr/ml) |
|---|---|---|---|
| Non-adjusted pH | A1 | 2836 | 4352.3 |
| High pH | A1 | 2492.4 | 2543.9 |
| Non-adjusted pH | A2 | 451.77 | 2054 |
| High pH | A2 | 3497.4 | 5880.5 |
| Non-adjusted pH | A3 | 486.84 | 2025.7 |
| High pH | A3 | 7252.9 | 11346 |

Example 4

Oral Absorption of Rigosertib in Dogs after Dosing with Rigosertib Formulation Prepared Using Different Lots of API Introduction Rigorsertib (ON 01910.Na) oral solutions were dosed to fasted non-naïve male beagle dogs and the absorptions were compared among three formulations.

Experimental Procedure

Three formulation of oral Rigosertib solutions were prepared:

C. ON 01910.Na 75 mg/mL non-pH adjusted concentrate (final pH by USP <791>: 6.98; API Batch #: ONA1LA03J)

D. ON 01910.Na 75 mg/mL high pH concentrate (final pH by USP <791>: 9.82; API Batch #: ONA1LA03J)

E. ON 01910.Na 75 mg/mL high pH concentrate (final pH by USP <791>: 9.80; API Batch #: ONA1NA04J)

Preparation of Drug Product Formulation

ON 01910.Na (API Lot #ONA1LA03J) non-pH adjusted concentrate was prepared by simply adding ON 01910.Na API slowly into PEG 400 solution and stirred using overhead stirring until a homogenous solution was obtained. The drug product was then filtered through 0.45 µm membrane filter. The pH of final drug product was measured by dilution method (final pH is 6.98) and then stored at refrigerated condition.

The high pH formulations was prepared by adding 4.0 N NaOH into PEG 400 vehicle first and then adding weighed amount of ON 01910.Na API slowly and mixing for ~2 hrs until a homogenous solution was obtained. The pH of the solution was measured by USP<791> dilution method and further adjusted with 4.0 NaOH until pH close to 10 was achieved. The drug product was then filtered through membrane filter and the final pH was measured by dilution method. The drug product was then filtered through 0.45 µm membrane filter and stored under refrigerated condition before use. In the pH adjusted formulation, two different lots of API (Lot #: ONA1LA03J and ONA1NA04J) were used in order to compare whether the API has any impact on absorption.

Animal Dosing and Blood Collection

All animals were fasted overnight before single oral administration at 25 mg/kg via oral placement. Approximately 1.0 mL whole blood was collected into a tube containing $K_2EDTA$ via jugular vein. At pre-dose, approximately 10 mL whole blood was collected. Approximately 30 minutes post collection, the blood was gently mixed to assure distribution of the anti-coagulant. Immediately after the blood sample was collected and mixed it was placed on wet ice or refrigerated and then be centrifuged refrigerated at 4-8° C. for 10 minutes at approximately 3,000 rpm. Plasma was harvested and stored frozen at approximately −80° C. within two hours from sample collection. Detailed study design is described below (Table 5).

TABLE 5

Study Design

| Group # | Animal # | Test article | Dosage Level (mg) | Dose Route | Dosing Schedule | Blood Collection Times (hr) |
|---|---|---|---|---|---|---|
| 1 | 3 | ON01910.Na 75 mg/mL Regular pH (A) | 25 mg/kg | PO | Once, Day 1 | Predose*, 0.5, 1, 2, 4, 8, 12 and 24 hr |
| | | 96-Hour Washout Period | | | | |
| 2* | 3 | ON01910.Na 75 mg/mL High pH-LA03J (B) | 25 mg/kg | PO | Once, Day 5 | Predose*, 0.5 1, 2, 4, 8, 12 and 24 hr |
| | | 72-Hour Washout Period | | | | |
| 3* | 3 | ON01910.Na 75 mg/mL High pH-NA04J (C) | 25 mg/kg | PO | Once, day 8 | Predose*, 0.5, 1, 2, 4, 8, 12 and 24 hr |

*The same animals from group 1 were be dosed for groups 2 and 3

Drug Concentration Determination by LC-MS/MS Method

The drug concentration in dog plasma samples was determined through multiple reaction monitoring (MRM) by an in-house developed LC-MS/MS assay with calibration range of 10-5000 ng/mL for ON 01910 as described above for Example 3.

Results

The Cmax and AUC of ON 01910 after dosing with three different ON 01910.Na drug product solutions for the individual dogs are shown in Table 5. The data showed that the dogs showed higher absorption in dogs administered orally with high pH formulation compared to regular pH formulation independent of the lot of drug substance used in the formulation.

TABLE 6

Oral Absorption of Rigosertib in Dogs - Dose - 25 mg/kg; n = 3

| Formulation | Animal Number | Cmax (ng/ml) | AUC (ng-hr/ml) |
|---|---|---|---|
| Non-adjusted pH | A1 | 1014.08 | 2194.83 |
| High pH-LA03J (B) | A1 | 4482.98 | 7468.25 |
| High pH-NA04J (C) | A1 | 2341.79 | 4348.10 |
| Non-adjusted pH | A2 | 678.98 | 1933.29 |
| High pH-LA03J (B) | A2 | 372.03 | 928.82 |
| High pH-NA04J (C) | A2 | 2826.25 | 5504.01 |
| Non-adjusted pH | A3 | 3521.29 | 5351.44 |
| High pH-LA03J (B) | A3 | 4212.17 | 3828.17 |
| High pH-NA04J (C) | A3 | 5312.99 | 7362.67 |

Example 5

Oral Absorption of Rigosertib in Dogs after Dosing with Three Different Capsules Introduction Three different forms of Rigorsertib (ON 01910.Na) oral formulation were dosed to beagle dogs and the absorptions were compared among different formulations.

Experimental Procedure

Three formulation of oral Rigosertib were prepared:
A. Enteric enTRinsic™ capsules filled with 280 mg ON 01910.Na API powder
B. Enteric enTRinsic™ capsules filled with 140 mg ON 01910.Na high pH formulation
C. Softgel Capsules filled with 280 mg ON 01910.Na non-pH adjusted formulation (Pii batch #: 19702.008A)

Preparation of High pH Drug Product Formulation

The high pH formulation was prepared as follows (for 200 mL drug formulation):

Weigh 169.46 g of PEG 400 (Croda Super refined PEG 400) into a 500 mL beaker. The initial pH was determined to be 5.90 using direct probe with stirring (Metrohm cat. #: 6.0229.010). After adding 0.5 mL 4.0 N NaOH and stirred for ~30 minute at room temperature, the pH was determined to be 13.39. Then 57.14 g of ON 01910.Na drug substance (Lot #: 14208344) was added slowly into the pH adjusted PEG 400. The mixture was stirred at 700 rpm for ~1 hour until a homogenous suspension was obtained. The pH was measured to be 10.31 by direct probe method. The process of adding 4.0 N NaOH and measuring its pH again after ~30 minutes stirring each time was repeated until the pH was between 12.30-13.00 by direct probe method. The total amount of 4.0 N NaOH added was ~0.6 mL and the final pH of the drug product solution was 12.69. The total mixing time was ~3 hours. The pH adjusted formulation was filtered through 250 μM sieves to get a clear light yellow solution. The final pH of the filtered drug product was 12.26. Store the final drug product in glass vials under refrigerated condition. The final concentration of the formulation was 280 mg/ml.

Capsule Filling

For formulation A, weigh 280 mg of ON 01910.Na drug substances powder carefully and manually fill into the empty enTRinsic capsules. Close the cap. For formulation B, transfer 0.56 g of high pH formulation, containing about 140 mg of drug, by syringe into the empty enTRinsic capsules. Close the cap. The softgel of Formulation C contains 1 mL of non-pH adjusted formulation containing about 280 mg of drug.

Preparation of 280 mg Oral ON 01910.Na (Rigosertib) Soft Gelatin Capsules (Formulation C)

Soft gelatin capsules of Rigosertib were composed of ON 01910.Na yellow colored oblong shaped opaque capsules containing a thick clear solution. These capsules additionally contained Gelatin, NF; Glycerin, USP; Sorbitol Sorbitan Solution, NF; Opatint White (G-18000); FD&C Yellow #6 powder; D&C Yellow #10; and Purified Water, USP. Rigosertib capsules were manufactured in 280 mg strength as follows. Each 280 mg strength capsule weighing 1000 mg contained 280 mg ON 01910.Na dissolved in 673.4 mg Polyethylene Glycol 400, NF, (Dow Chemical Company); 20 mg Polyethylene Glycol 4000, NF, (Dow Chemical Company) and 26.6 mg purified water, USP.

The manufacturing process for the 280 mg drug product involved adding ON 01910.Na to PEG 400, in a stainless steel container under a nitrogen blanket. The product was homogenized at 15° C. to 20° C. until the excipients and the drug were completely dispersed. The product was held at room temperature for 9 to 12 hours and then was checked visually for any un-dissolved particles. If un-dissolved particles were present, the contents were homogenized in an ice bath or chiller for 30 to 60 minutes. The contents were then passed through a #40 mesh hand screen and then all screened material was collected. The product was vacuum deaerated for not less than an hour and until no air bubbles were observed. The product was then encapsulated, dried and inspected visually to remove leakers, odds, under fills, and stickiness.

Animal Dosing and Blood Collection

Nine male Beagle dogs were assigned into three groups (3 dogs/Group). All animals were fasted overnight before single oral administration with capsules of 280 mg flat dose. Approximate 1.0 mL whole blood was collected into a tube containing $K_2EDTA$ via jugular veins or limb veins except that 2 mL whole blood was drawn from each dog at predose. The blood was gently inverted to assure even mixing with the anti-coagulant. Immediately after the blood sample was collected and mixed, it was placed on wet ice or ice packs, and centrifuged refrigerated at 4-8° C. for 10 minutes at approximately 3,000 rpm. Plasma was then harvested into pre-labeled snap-top 1.5 mL tubes and stored frozen at approximately −80° C. within two hours from sample collection. Detailed dosing regimen is described below (Table 7).

TABLE 7

Study Design

| Group # | Animal # | Test article | Formulation | Dosage Level (mg) | Dose Amount | Dosing route and regimen | Blood Collection Times |
|---|---|---|---|---|---|---|---|
| 1 | 1001 1002 1003 | ON01910.Na | enTRinsic capsules filled with powder | 280 mg | 1 x 280 mg | PO, Once a day | Predose*, 0.5, 1, 2, 4, 8, 12 and 24 h. |
| 2 | 2001 2002 2003 | ON01910.Na | enTRinsic capsules filled with high pH formulation | 280 mg | 2 x 140 mg | PO, Once a day | Predose*, 0.5 1, 2, 4, 8, 12 and 24 h. |
| 3 | 3001 3002 3003 | ON01910. Na | Softgel | 280 mg | 1x 280 mg | PO, Once a day | Predose*, 0.5, 1, 2, 4, 8, 12 and 24 h. |

Comments *2 ml whole blood will be drawn from each dog at predose for matrix.

Drug Concentration Determination by LC-MS/MS Method

The drug concentration in plasma samples was determined through multiple reaction monitoring (MRM) by a validated LC-MS/MS assay with calibration range of 10-10,000 ng/mL for ON 01910 and 1-1000 ng/mL for its potential metabolite ON 01500. Briefly, samples were extracted by protein precipitation method using four volumes of acetonitrile. After vortex the samples were centrifuged at 14,000 rpm for 10 minutes. The supernatant was then further diluted three fold with 20% ACN/80% $H_2O$ and 3 μL was injected into AB Sciex API-4000 LC/MS/MS system for analysis. The mobile phase A (MPA) is 10 mM ammonium acetate in water and the mobile phase B (MPB) is 0.1% formic acid in acetonitrile. The samples were separated by isocratic elution with 55% MPB on Hypersil BDS C18 column (5 μm, 100×2.1 mm). The flow rate used was 0.25 mL/min and then changed to 0.5 mL/min from 2.6 to 4.4 minutes for washing the column. The total run time was 5.1 minutes.

Results

The concentrations of ON 01910 after dosing with three different oral formulation were plotted versus dosing time in FIG. 2. The pharmacokinetic parameter Cmax were calculated and summarized in Table 8. The data showed that the exposure to drug increased by ~1.7 fold in dogs dosed with enTRinsic capsules filled with high pH formulation compared to the current non-pH adjusted clinical dosing form in softgel. The exposure in enTRinsic capsules filled with API powder is very low.

TABLE 8

Oral Absorption of Rigosertib in Dogs - New Formulation in Capsules
Dose - 280 mg; n = 3

| Parameter | Formulation A Powder in Capsule | Formulation C Softgel | Formulation B New pH Adjusted Formulation in Capsule |
|---|---|---|---|
| AUC (ng-hr/ml) | 673.20 ± 457.45 | 6700.30 ± 354.53 | 11833.30 ± 2398.17 |

Summary

The dog study showed the oral formulation of enTRinsic capsules filled with high pH formulation will increase the drug exposure by ~1.7 fold compared to softgel capsule filled with non-pH adjusted formulation.

Example 6

Treatment Protocol Using Rigosertib Concentrate for Infusion

Rigosertib Concentrate is a sterile, concentrated solution in labeled, sealed glass vials, which must be stored between 2° C. and 8° C. Just prior to dosing, the rigosertib concentrate should be thawed and diluted in 0.9% sodium chloride for injection. Reconstituted rigosertib must be kept at room temperature and administration must start within 6 hours of reconstitution, through a port or central line using an infusion pump with an in-line filter.

Rigosertib labels will contain information to meet applicable regulatory requirements. Rigosertib 1800 mg/24 hr administered as a 72-hr CIV infusion on Days 1, 2, and 3 of a 2-week cycle for the first 8 cycles, and on Days 1, 2, and 3 of a 4-week cycle thereafter. Infusion bags must be changed every 24 hours and a new infusion bag must be used for each of the subsequent 24 hours until completion of the total 72-hour infusion time.

How Supplied

The investigational agent ON 01910.Na Concentrate, 75 mg/mL is formulated to contain 75 mg of ON 01910.Na per mL (equivalent to 75 mg of rigosertib sodium per mL) as a sterile solution in Polyethylene Glycol 400 (PEG 400) containing a small amount of Sodium hydroxide for pH adjustment. ON 01910.Na Concentrate, 75 mg/mL is packaged in single-use glass vials with Teflon-lined rubber stoppers containing 24 mL of drug product (1800 mg). Sites will be provided cartons containing 25 vials of ON 01910.Na Concentrate.

Storage Guidelines for ON 01910.Na Concentrate, 75 mg/mL

The vials should be stored refrigerated (2° to 8° C.) in their original storage cartons to protect them from light.

It is normal for the contents of the vials, when properly stored at 2° to 8° C., to appear to be either in a solid or a liquid state. When the vials are warmed to room temperature in preparation for dilution, the contents of the vials should be a clear, colorless to yellowish, slightly viscous liquid.

Dilution of ON 01910.Na Concentrate for Administration

1. ON 01910.Na Concentrate, 75 mg/mL must be diluted before administration with 0.9% Sodium chloride, USP.
2. Before preparing the dilution, remove vial(s) from the refrigerator and let them stand at room temperature for 30 to 60 minutes, and then gently mix the contents of the vial(s). Vials should never be warmed above ambient temperature.
3. ON 01910.Na Concentrate, 75 mg/mL, contains no antimicrobial preservative. Strict aseptic technique must be followed to prepare the dilution.
4. Dilute the volume of ON 01910.Na Concentrate, 75 mg/mL required for the prescribed dose (see Table 9) with 0.9% Sodium Chloride, Concentrate to a final volume of 500 mL in an infusion bag. It is recommended to use infusion bags that are free of latex and DEHP. Bags that protect from light are recommend, if your site holds these routinely.
5. Gently invert the infusion bag several times to insure that the ON 01910.Na Concentrate is completely and evenly mixed with the 0.9% Sodium Chloride. (The density and viscosity of the PEG 400 vehicle may affect mixing).
6. Inspect the infusion solution visually for particulate matter and discoloration prior to use. The resulting solution should be clear and colorless or slightly yellow.
7. Once the infusion solution is prepared, it is stable for 30 hours at room temperature. Therefore, once the infusion solution is prepared, administration of the infusion must start within 6 hours. A fresh batch of infusion solution must be prepared for each 24-hour segment of the continuous 72-hour infusion regimen and a new IV bag and infusion set should be used for each fresh batch. Three batches of 500 mL infusions are needed to complete the 72-hour regimen.
8. Administer each 500 mL infusion over 24 hours using an infusion pump that has medication error-prevention software to alert operators and patients when the pump operating outside of the desired pre-configured limits. Infusions should be given through an administration set with an in-line filter with a pore size between 0.2 and 1.2 microns.
9. If there is a small interruption, the infusion should be re-started to deliver the remaining rigosertib. The infusion rate may need to be increased to deliver the remainder within 24 hrs, if the subject can tolerate the increase (i.e. the remainder can be delivered if within the 30 hr stability window). If there is a large amount of rigosertib left over, due to a long interruption, the volume infused should be entered into EDC and the next bag started (due to stability). A new bag may be prepared on Day 4 to deliver the missed rigosertib.
10. Do not mix other drugs with the ON 01910.Na Concentrate in the IV bag or administer other drugs concurrently with ON 01910.Na through the same line.

TABLE 9

Use these volumes to prepare 500 mL infusion solution
of ON 01910.Na Concentrate for each 24-hour infusion

| Dose | Volume (mL) of ON 01910.Na Concentrate, 75 mg/mL |
|---|---|
| 1800 mg/24 hr | 24 |
| 1350 mg/24 hr* | 18 |
| 900 mg/24 hr* | 12 |

*These doses are to be used in the event dose reductions are required according to Protocol.

Example 7

Treatment Protocol Using Oral Rigosertib Capsule Alone and in Combination with Azacitidine to Reduce Urothelial Toxicity A soft gelatin capsule of Rigosertib was manufactured under cGMP. The composition of the fill material of the capsule is listed as follows:

| Ingredient | Amount per capsule (mg) |
| --- | --- |
| Rigosertib | 280 |
| Polyethylene Glycol 6000 | 20 |
| Polyethylene Glycol 400 | 673.40 |
| Purified Water | 26.60 |

The composition of the wet shell material is as follows:

| Ingredient | Amount per capsule (mg) |
| --- | --- |
| Bovine Gelatin 150 bloom | 42.073 |
| Glycerine | 10.664 |
| Sorbitan Sorbitol Solution NF | 14.024 |
| Titanium dioxide | 0.324 |
| FD&C Yellow 6 | 0.008 |
| Purified Water | 32.907 |

The soft gelatin capsules of the above composition were manufactured using standard method known in the art and used in the following studies.

Summary of Clinical Protocols:

Study Comparing Continuous and Intermittent Administration

Soft gelatin capsule of Rigosertib was tested in this phase 2 study in LR (Lower Risk intermediate-1 or low risk per IPSS classification) transfusion-dependent MDS patients. The capsules (560 mg) were administered twice a day, under fasting conditions, approximately 12 hours apart. The total dose of drug was 1120 mg per day. Various treatment regimens were tested:

Continuous administration, i.e 4 out of 4 weeks. 9 patients were treated.
Intermittent administration; i.e 2 weeks on and one week off. 35 patients were treated.

Continuous rigosertib dosing cohort was discontinued early due to high urinary adverse events (AEs). Intermittent administration was better tolerated than the continuous administration but the percentage of incidence of urinary adverse events was still problematic. Thus, even with Intermittent administration, there was still a need for an improved dosing regimen that reduced urinary adverse events.

Study of Shorter Spacing Between Two Doses: Phase II, Part 2 (Expansion) (N=up to 40 evaluable patients):

This study was conducted in patients with high risk MDS. RAEB-t (Refractory Anemia with Excess Blasts in Transformation)/non-proliferative AML were eligible but patients with CMML (Chronic Myelomonocytic Leukemia) were excluded.

The Phase II, Part 2 component of the study consisted of 2 cohorts of up to 40 evaluable patients randomized 1:1 into 2 cohorts of up to 20 patients each to receive 1120 mg of rigosertib over 24 hours: either 560 mg in the morning before breakfast in the fasting state and 560 mg in the afternoon, or 840 mg in the morning before breakfast in the fasting state and 280 mg in the afternoon. The afternoon dose in both cohorts must be administered at 3 PM (±1 hr) at least 2 hours after lunch. Each cohort will be stratified among HMA (hypomethylating agents) naïve and HMA refractory patients.

Treatments Administered:

Each patient was required to complete a diary indicating the day and time of drug intake and record daily urinary dipstick pH and microscopic hematuria test. Rigosertib was supplied as 280 mg and 70 mg (in the event that different doses are needed) capsules by Onconova. Patients took oral rigosertib as an intermittent regimen (3 weeks-on, 1 week-off). Rigosertib was administered on an outpatient basis unless the patient was inpatient for another reason. The oral rigosertib administration preceded administration of azacitidine ("AZA") by 7 days. Rigosertib should be taken in a fasting state twice daily. Patients were instructed to take their morning dose after an overnight fast, on an empty stomach, and wait 1 hr after dosing to have breakfast. The afternoon dose should be taken at approximately 3 PM (±1 hr) at least 2 hr after lunch, on an empty stomach, and patients should wait 1 hr before the next meal. The afternoon dose was taken about 6 to 8 hours after the first dose. Water was permitted during the fasting period. Good hydration (ie, at least 2 liters of water per day) was recommended for all patients. It was also recommended that patients void their bladder before bed. If patients tested the pH of their urine about 2 hours after the morning dose and the pH was less than 7.5, it was suggested that patients take 650 mg of sodium bicarbonate three times a day.

Starting on Day 8, AZA was administered by SC injection or IV infusion at a 75 mg/m$^2$ daily dose for 7 days of a 28-day cycle.

Criteria for Evaluation:

Safety assessment: medical history, physical examination, vital signs (blood pressure, temperature, respiration rate, and pulse), weight, standard 12-lead ECG, laboratory evaluations, and toxicity and AE assessments were monitored throughout the study. Urinary Adverse Events are pollakiuria, micturition urgency, urinary tract pain, hematuria and dysuria.

Results: The data in Table 10 demonstrate a dramatic reduction in the incidence of urinary adverse events when the drug is administered about 8 hours apart.

TABLE 10

| Parameter/Treatment | | |
| --- | --- | --- |
| Single Agent Rigo Intermittent (2 weeks on/1 week off) | Rigosertib in Combo with AZA Shorter Spacing Between First and Second Dose | |
| Dose & Regimen | | |
| 560 mg bid q12 hrs | 560 mg bid q8 hrs | 840/280 mg bid q8 hrs |
| Incidence of Urinary AEs (% of Patients) | | |
| Total patients (n) 35 | 19 | 18 |
| Grade 1/2  25 (71) | 5 (26) | 5 (28) |
| Grade 3  8 (23) | 0 (0) | 2 (11) |

All references cited herein, including patents, patent applications, and publications, are hereby incorporated by reference in their entireties, whether previously specifically incorporated or not.

The various features and embodiments of the present invention, referred to in individual sections above apply, as appropriate, to other sections, mutatis mutandis. Consequently, features specified in one section may be combined with features specified in other sections, as appropriate.

The foregoing description of some specific embodiments provides sufficient information that others can, by applying current knowledge, readily modify or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. In the drawings and the description, there have been disclosed exemplary embodiments and, although specific terms may have been employed, they are unless otherwise stated used in a generic and descriptive sense only and not for purposes of limitation, the scope of the claims therefore not being so limited. Moreover, one skilled in the art will appreciate that certain steps of the methods discussed herein may be sequenced in alternative order or steps may be combined. Therefore, it is intended that the appended claims not be limited to the particular embodiment disclosed herein. Those skilled in the art will recognize, or be able to ascertain using no more than routine experimentation, many equivalents to the embodiments of the invention described herein. Such equivalents are encompassed by the following claims.

What is claimed is:

1. A pharmaceutical composition comprising,
    a) (E)-2,4,6-trimethoxystyryl-3-[(carboxymethyl)amino]-4-methoxybenzylsulphone and pharmaceutically acceptable salts thereof;
    b) basic pre-treated low molecular weight polyethylene glycol comprising one or more of PEG 200, PEG 300, PEG 400, PEG 600, and/or PEG 800;
    c) undiluted pH of about 11.0 to about 14.0; and
    d) less than 5% water or aqueous solution.

2. An oral dosage form comprising the pharmaceutical composition of claim 1 having about 35 to about 400 mg of (E)-2,4,6-trimethoxystyryl-3-[(carboxymethyl)amino]-4-methoxybenzylsulphone, sodium salt in each oral dosage form.

3. A method of treating conditions mediated by abnormal cell proliferation comprising administering an effective amount of the pharmaceutical composition of claim 1 to a subject in need thereof.

4. The method of claim 3 wherein said condition is selected from hematological cancer.

5. The method of claim 4 wherein said hematological cancer is selected from AML and MDS.

6. The method of claim 5, wherein said pharmaceutical composition is in an oral dosage form comprising 70 mg to 280 mg (E)-2,4,6-trimethoxystyryl-3-[(carboxymethyl)amino]-4-methoxybenzylsulphone, sodium salt per dosage form.

7. The method of claim 6, wherein said pharmaceutical composition is in an oral dosage form comprising 280 mg (E)-2,4,6-trimethoxystyryl-3-[(carboxymethyl)amino]-4-methoxybenzylsulphone, sodium salt per dosage form and said oral dosage form is administered in a dose of about 280 mg to 840 mg twice per day to said subject.

8. A method of treating conditions mediated by abnormal cell proliferation comprising administering an effective amount of (E)-2,4,6-trimethoxystyryl-3-[(carboxymethyl)amino]-4-methoxybenzylsulphone, sodium salt to a patient in need thereof, comprising orally administering a first dose of 70-840 mg approximately 1-2 hours before breakfast, and a second dose of 70-560 mg administered in the fasting state about 6 to about 8 hours after the first dose.

9. The method of claim 8 wherein said patient is administered (E)-2,4,6-trimethoxystyryl-3-[(carboxymethyl)amino]-4-methoxybenzylsulphone, sodium salt for three weeks followed by one week off and said patient is also administered azacitidine starting at day 8 for one week.

10. The method of claim 8 wherein said condition is a hematological cancer.

11. The method of claim 10 wherein said hematological cancer is selected from the group consisting of AML and MDS.

12. The method of claim 8 wherein the first dose is selected from 70 mg, 140 mg, 280 mg, 560 mg, 700 mg, and 840 mg, and the second dose is selected from 70 mg, 140 mg, 280 mg, and 560 mg.

13. The method of claim 12 wherein the first dose is selected from 280 mg, 560 mg, and 840 mg, and the second dose is selected from the group selected from 280, and 560 mg, and said condition is a hematological cancer.

14. The method of claim 8 wherein the first dose is 840 mg and the second dose is 280 mg, or wherein the first dose is 560 mg and the second dose is 280-560 mg.

* * * * *